United States Patent [19]

Bradford et al.

[11] Patent Number: Plant 7,070

[45] Date of Patent: Dec. 12, 1989

[54] PEACH TREE (CROWN PRINCESS)

[76] Inventors: Norman G. Bradford, 11875 E. Savana Rd.; Lowell G. Bradford, 12439 E. Savana Rd., both of Le Grand, Calif. 95333

[21] Appl. No.: 294,822

[22] Filed: Jan. 9, 1989

[51] Int. Cl.[4] ..... A01H 5/00

[52] U.S. Cl. ..... Plt./43

[58] Field of Search ..... Plt./43

*Primary Examiner*—Robert E. Bagwill

[57] ABSTRACT

The present invention relates to a peach tree and more particularly to a new and distinct variety broadly characterized by a large size, vigorous, hardy, productive and regular bearing tree. The fruit matures under the ecological conditions described approximately the first week in June, with first picking on June 3, 1988. The fruit is uniformly large in size, good in flavor, attractively oblate in shape, clingstone in type, very firm in texture making excellent quality for keeping and shipping, and almost full red in skin color at harvest time. The variety was developed as a hybridized seedling from the selected seed parent, Red Diamond (U.S. Pat. No. P.P. 3,165) nectarine, and an unnamed peach seedling as the selected pollen parent.

1 Drawing Sheet

BACKGROUND OF THE VARIETY

In a continuing effort to improve the quality of shipping fruits, we, the inventors, typically hybridize a large number of nectarine, peach, plug, apricot, and cherry seedlings each year. The present invention relates to a new and distinct variety of peach tree, which has been denominated varietally as "Crown Princess". The present variety was hybridized in 1984 by us in a cultivated area of our experimental orchard at Bradford Farms near Le Grand, Calif. in Merced County (San Joaquin Valley). It was the result of a seedling using Red Diamond (U.S. Pat. No. P.P. 3,165) nectarine as the selected seed parent and an unnamed peach seedling as the selected pollen parent. Subsequent to origination of the present variety of peach tree, we asexually reproduced it by budding and grafting, and such reproduction of plant and fruit characteristics were true to the original plant in all respects.

The fruit produced by the present variety matures at nearly the same time as that of Merrill Gemfree (U.S. Pat. No. P.P. 1,409) peach, but is distinguished therefrom and an improvement thereon by having almost full red skin color at ripening time, by being extremely firm and non-melting in texture, by being clingstone in type, and by having a more desirable oblate shape.

The present invention exhibits desirable characteristics common to its selected seed parent, Red Diamond (U.S. Pat. No. P.P. 3,165) nectarine, by producing fruit that is nearly full red in color at harvest time and very firm in texture. It noticeably differs from the Red Diamond by being a peach instead of a nectarine, by being clingstone instead of freestone, and by having a large blossom instead of a small blossom.

DRAWING

The accompanying photograph shows the characteristics of the whole fruit in skin color and form, a characteristic fruit divided on its suture plane showing the flesh and pit cavity, a typical stone, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of shipping ripe on June 3, 1988. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed.
Hardiness: Hardy.
Production: Productive.
Bearing: Regular bearer.
Trunk:
- *Size.*—Medium.
- *Texture.*—Medium.
- *Bark color.*—Moderate yellowish brown [77. m.yBr].
- *Lenticels.*—Numerous. Color: Dark orange yellow [72. d.OY]. Size: 1/16" to ¼", [1.588–6.35 mm.].

Branches:
- *Size.*—Medium.
- *Texture.*—Medium.
- *Color.*—1st Year wood — Topside: Brilliant yellow green [116. brill.YG] with some grayish pink [8. gy.Pk] tinting. 1st Year wood — Underside: Brilliant yellow green [116. brill.YG]. Older wood: Dark yellowish brown [78. d.yBr].
- *Lenticels.*—Few, very small.

Leaves:
- *Size.*—Large. Average length: 6⅛" [155.6 mm.]. Average width: 1 9/16" [39.69 mm.].
- *Thickness.*—Medium.
- *Form.*—Elliptical.
- *Apex.*—Acuminate.
- *Base.*—Acute.
- *Surface.*—Smooth.
- *Color.*—Dorsal Surface: Moderate olive green [125. m.01G]. Ventral Surface: Moderate yellow green [120. m.YG].
- *Margin.*—Finely serrate.

*Venation.*—Pinnately net veined.

*Petiole.*—Average length: ½" [12.7 mm.]. Average thickness: 1/16" [1.59 mm.]. Color: Moderate yellow green [120. m.YG].

*Stipules.*—Numerous. Average Length: ¼" [6.35 mm.]. Glands: Numbers: Mostly 2 to 4 per leaf. Position: Some oppositely and some alternately positioned on petiole and base of blade. Size: Medium. Form: Globose. Color: Light grayish red [18. 1.gy.R].

Flower buds:

*Hardiness.*—Hardy.

*Size.*—Medium.

*Length.*—Medium.

*Form.*—Free.

*Surface.*—Pubescent.

Flowers:

*Blooming period.*—Medium as compared with other varieties.

*Size.*—Large.

*Color.*—Pale pink [7. p.Pk].

FRUIT

Maturity when described: Shipping ripe, June 3, 1988.

Date of first picking: June 3, 1988.

Date of last picking: June 10, 1988.

Size: Uniform, large.

*Average diameter axially.*—2⅝" [66.68 mm].

*Average transversely in suture plane.*—2½" [63.5 mm].

Form: Uniform, symmetrical, globose to oblate with some truncation at both the apex and base.

*Longitudinal section form.*—Oblate.

*Transverse section through diameter.*—Round, with a slight hump at the suture.

Suture: A shall depression extending from the base but discontinuous at the apex.

Ventral surface: Rounded, lipped toward apex.

Lips: Slightly protruded along the suture, slightly unequal.

Cavity: Flaring, elongated in the suture plane, suture showing on one side only.

Base: Cuneate and truncate.

Apex: Rounded and slightly truncate.

Pistil point: Mostly oblique, short in length.

Stem: Medium.

*Average length.*—⅜" [9.53 mm.].

*Average width.*—3/16" [4.76 mm.].

Skin:

*Thickness.*—Medium.

*Texture.*—Medium.

*Tenacity.*—Tenacious to flesh.

*Tendency to crack.*—Slight in wet season.

*Color.*—Dark red [16. d.R] toward the apex end with streaking into a dark pink [6. d.Pk] background at the stem end.

Down: Scant, short, does not roll up when rubbed.

Flesh:

*Color.*—Brilliant yellow [83. brill.Y] to the pit.

*Amygdalin.*—Scarce.

*Juice.*—Abundant, rich.

*Texture.*—Very firm, non-melting.

*Fibers.*—Abundant, fine, tender.

*Ripens.*—Evenly.

*Flavor.*—Mildly subacid.

*Aroma.*—Moderate.

*Eating quality.*—Very good.

STONE

Type: Clingstone.

Form: Oval.

Base: Straight.

Apex: Acute.

Sides: Equal.

Surface: Irregularly furrowed throughout.

Ridges: Jagged toward apex.

Color: Light yellowish brown [76. 1.yBr].

Pit wall: 7/32" [5.56 mm.] thick.

Tendency to split: Slight.

Kernel:

*Form.*—Oval.

*Taste.*—Bitter.

*Viable.*—Yes.

*Average width.*—½" [12.7 mm.].

*Average length.*—⅝" [15.88 mm.].

Pellicle color: Light yellowish brown [76. 1.yBr].

Amygdalin: Abundant.

USE

Market: Fresh and long distance shipping.

Keepling quality: Excellent.

Shipping quality: Excellent.

Resistance to insects: No unusual susceptibilities noted.

Resistance to diseases: No unusual susceptibilties noted.

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct early ripening variety of clingstone peach tree, substantially as illustrated and described, which most nearly resembles the Merrill Gemfree (U.S. Pat. No. P.P. 1,409) peach variety by producing fruit that matures at nearly the same time, but is distinguished from and an improvement on that variety by having almost full red skin color at ripening time, by being extremely firm and non-melting in texture, by being clingstone in type, and by having a more desirable oblate shape.

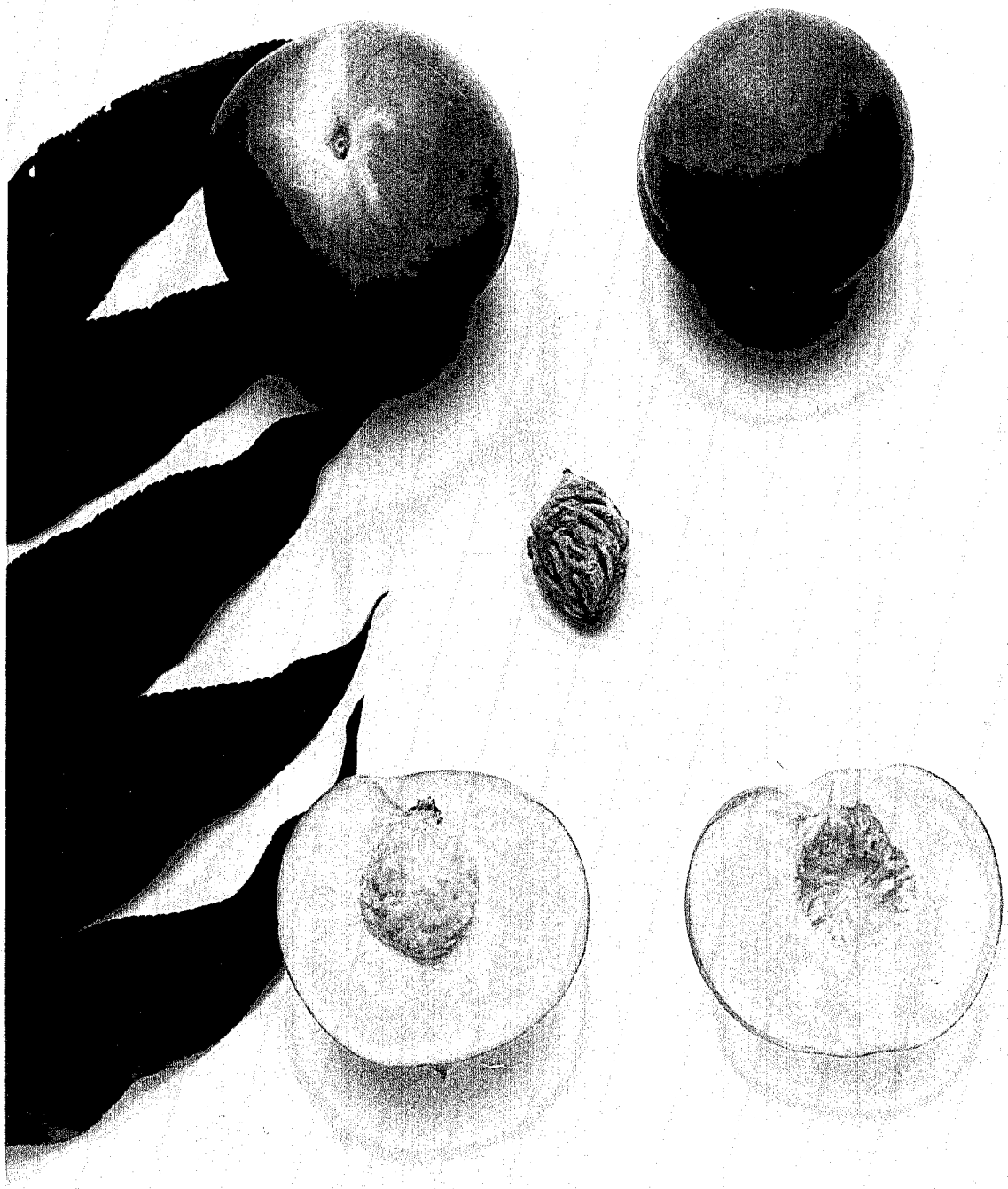

* * * * *